United States Patent [19]

Ortiz et al.

[11] Patent Number: 5,358,496
[45] Date of Patent: Oct. 25, 1994

[54] ENDOSCOPIC TISSUE MANIPULATOR

[75] Inventors: Mark S. Ortiz, Milford, Ohio; M. Joshua Tolkoff, Brookline; William W. Malecki, Newton; Fernando A. de Toledo, Concord, all of Mass.

[73] Assignee: Ethicon, Inc., Somerville, N.J.

[21] Appl. No.: 130,162

[22] Filed: Sep. 30, 1993

Related U.S. Application Data

[63] Continuation of Ser. No. 780,697, Oct. 18, 1991, abandoned.

[51] Int. Cl.$^5$ .................................................. A61M 29/00
[52] U.S. Cl. ................................. 606/198; 604/104
[58] Field of Search ............... 606/198, 191, 106–108, 606/127, 128; 604/104–107

[56] References Cited

U.S. PATENT DOCUMENTS

| | | | |
|---|---|---|---|
| 872,217 | 11/1907 | Bonesteel | 604/104 |
| 1,878,671 | 9/1932 | Cantor | 606/191 |
| 2,067,031 | 1/1937 | Wappler | 606/198 |
| 3,517,128 | 2/1968 | Hines | 606/198 |
| 3,857,395 | 12/1974 | Johnson et al. | 606/198 |
| 4,590,938 | 5/1986 | Segura et al. | 606/127 |
| 4,625,726 | 12/1986 | Duthoy | 606/127 |
| 4,654,028 | 3/1987 | Suma | 604/106 |
| 4,655,219 | 4/1987 | Petruzzi | 606/206 |
| 4,705,041 | 11/1987 | Kim | 606/108 |
| 4,744,363 | 5/1988 | Hasson | 128/321 |
| 4,807,626 | 2/1989 | McGirr | 604/107 |
| 4,909,789 | 3/1990 | Taguchi et al. | 606/198 |
| 4,997,435 | 3/1991 | Demeter | 606/127 |
| 5,041,093 | 8/1991 | Chu | 606/198 |
| 5,113,846 | 5/1992 | Hiltebrandt et al. | 128/20 |

FOREIGN PATENT DOCUMENTS

| | | |
|---|---|---|
| 0449663 | 2/1991 | European Pat. Off. . |
| 0464463 | 8/1992 | European Pat. Off. . |
| 25796 | 1/1884 | Fed. Rep. of Germany . |

OTHER PUBLICATIONS

Medi-tech Catalog, copyright 1989, p. 911, entitled "Segura Baskets".
Microvasive Catalog, dated 1989, pp. 51–61, entitled "Segura Baskets".

Primary Examiner—Edgar S. Burr
Assistant Examiner—Anthony H. Nguyen

[57] ABSTRACT

A tissue manipulator is provided which is insertable through an endoscopic tube to enable a surgeon to manipulate tissue inside a body cavity. The tissue manipulator includes an expandable frame comprising a plurality of flexible, interconnected frame members which are adapted to expand laterally outward into a spatula-like platform for engaging the tissue. The platform is selectively expandable into a tulip-shaped configuration and a bulb-shaped configuration to manipulate large body organs such as the liver, lungs or intestines without risk of injury to such organs. The platform is infinitely adjustable in size from its collapsed configuration to its expanded configuration.

18 Claims, 7 Drawing Sheets

ENDOSCOPIC TISSUE MANIPULATOR

This is a continuation of application Ser. No. 780,697, filed Oct. 18, 1991, now abandoned.

FIELD OF THE INVENTION

The present invention relates to a tissue manipulator adapted for manipulating tissue in a human body and, more particularly, to an endoscopic tissue manipulator which is insertable through an endoscopic tube to enable a surgeon to manipulate tissue inside a body cavity. Also, the invention concerns an endoscopic tissue manipulator which is particularly suitable for use by a surgeon to displace large body organs, e.g., the liver, lungs, stomach or intestines, to enable surgery to be performed at a desired surgical site.

BACKGROUND OF THE INVENTION AND PRIOR ART

Endoscopic procedures have been developed for observing and treating internal body organs. Such procedures involve the insertion of an endoscope into a natural body orifice or through an incision in the body which allows a surgeon to observe and treat tissue inside a body cavity. Flexible endoscopes have been developed for insertion into natural body orifices, e.g., through the mouth or into the rectum. Also, rigid endoscopes have been developed for insertion into the abdominal cavity or the thoracic cavity through incisions at the surface of the body. Typically, a trocar is inserted into a trocar sleeve or tube to facilitate the insertion of the trocar sleeve through an incision and its penetration through internal body tissue. After the trocar sleeve is positioned at a desired surgical site, the trocar is removed from the trocar sleeve to allow another instrument such as an endoscope or forceps to be inserted into the trocar sleeve and advanced into contact with the tissue at the surgical site. The observation and treatment of the tissue can be made difficult by large body organs, e.g., the liver, lungs or intestines, which must be displaced to provide access to the surgical site.

In the prior art, several types of instruments are known for manipulating internal body tissue. For example, U. S. Pat. No. 4,909,789 discloses observation assisting forceps including a set of expandable wires mounted on a shaft which is normally retracted into a sheath. When the shaft is advanced, the wires project out of the sheath and expand into a fan-shaped configuration in the same plane. The expanded wires can be used to set aside internal organs obstructing the observation with an abdominal cavity endoscope. The wires are provided at the tips with spherical members which prevent the organs from being hurt.

U. S. Pat. No. 4,654,028 discloses an incision opening expansion holder including a plurality of wires at the end of an inner tube which are three dimensionally expanded when projecting out of an outer tube to expand an incision of a blood vessel graft for purposes of inosculation. U.S. Pat. No. 4,705,041 discloses a tissue dilator comprising a catheter which supports an expandable member, e.g., a balloon or a scissor-like member. U. S. Pat. No. 1,878,671 discloses a dilator for opening a body cavity including an ovate head mounted on a wire received in a tube which is inserted into the body cavity. U.S. Pat. No. 4,655,219 discloses a tissue grasping accessory including a plurality of flexible grasping arms for use with an endoscopic instrument to grasp a tissue specimen. U.S. Pat. No. 4,590,938 discloses a device for removal of kidney stones through the working channel of an endoscope including a basket comprising four outwardly bowed, generally flat spring arms which are expandable into a bulbous shape and collapsed when retracted into a sheath. The relatively broad, flat surfaces of the spring strips deflect the kidney tissue surrounding the stone while the distally enlarged volume of the basket allows the surgeon to dislodge and capture the stone.

None of the above described devices are particularly suited for use in manipulating large body organs, e.g., the liver, lungs or intestines, away from a desired surgical site. Moreover, it appears that several of the devices may have a tendency to damage the tissue if attempted to be used to displace large body organs.

Accordingly, it is an object of the present invention to provide a tissue manipulator which is adapted to safely manipulate internal body tissue.

Another object of the invention is to provide a tissue manipulator for insertion through an endoscopic device to manipulate tissue such as large body organs in a body cavity.

It is also an object of the invention to provide an endoscopic tissue manipulator which is suitable for insertion through an endoscopic device into a body cavity for displacing or retaining large body organs, e.g., the liver, lungs or intestines, away from a desired surgical site.

SUMMARY OF THE INVENTION

The present invention achieves an improved tissue manipulator which is adapted for insertion through an endoscopic device into a body cavity to manipulate internal body tissue therein. The tissue manipulator includes an expandable frame which is particularly suitable for engaging large body organs, e.g., the liver, lungs or intestines, without risk of injury to such organs. The expandable frame allows the large body organs to be displaced away from a desired surgical site and to be constrained in a position which does not obstruct access to the desired surgical site. The frame is selectively expandable into different configurations for use in situations where a relatively large amount of space is available for tissue manipulation and where a relatively small space is available to accommodate the tissue manipulator.

In accordance with the invention, the tissue manipulator comprises a handle, a support shaft extending from the handle, an expandable frame mounted at the distal end of the support shaft, and means for expanding the frame into a suitable configuration for manipulating tissue. The frame comprises a plurality of frame members which are adapted to expand laterally outward into a spatula-like platform for engaging the tissue. Preferably, the frame members are adapted to expand bilaterally outward to form a platform of generally planar configuration. The frame members are selectively expandable into a tulip-shaped configuration for use where a large amount of space is available for receiving the tissue manipulator and into a bulb-shaped shaped configuration for use where a limited amount of space is available to receive the tissue manipulator.

A preferred embodiment of the tissue manipulator for insertion into an endoscopic tube for manipulating tissue in a body cavity comprises a handle, a support shaft extending from the handle, an actuator tube slidably mounted on the support shaft for longitudinal movement relative to the support shaft, and an expandable frame mounted at the distal end of the support shaft and connected to the actuator tube. The frame is collapsible for insertion through the endoscopic tube and is expandable by movement of the actuator tube relative to the support shaft to provide a platform for manipulating tissue in the body cavity. The frame includes a pair of expandable fingers each comprising a flexible outer strip secured to the distal end of the actuator tube and a flexible inner strip secured to the distal end of the support shaft. The inner and outer strips are joined together at a distal finger tip. The fingers are flexed laterally outward in opposite directions by axial movement of the actuator tube relative to the shaft to provide a spatula-like platform for engaging the tissue. The fingers are selectively expandable into a tulip-shaped configuration with the finger tips spread apart and into a bulb-shaped configuration with the finger tips together. The fingers are expanded into the tulip-shaped configuration by movement of the actuator tube proximally relative to the support shaft and into the bulb-shaped configuration by movement of the actuator tube distally relative to the support shaft.

In the preferred embodiment of the tissue manipulator, the expandable frame includes a connector sleeve slidably mounted on the inner strips and located at a position beyond the distal end of the actuator tube. A pair of elongated flexible struts extends from the connector sleeve. Each of the struts is secured to an intermediate portion of one of the outer strips and is flexed outwardly when the fingers are expanded. A guide tube extends distally from the connector sleeve for slidably receiving the inner strips therein. The guide tube serves to hold the inner strips together when the acutator tube is advanced to prevent misalignment and crossover of the finger tips.

Preferably, the tissue manipulator includes a collet mechanism on the handle for releasably engaging the actuator tube to retain the platform in an expanded configuration. A manually operated release button is provided on the handle for releasing the collet mechanism to disengage the actuator tube and allow the platform to return to its collapsed configuration. In addition, a sheath is slidably mounted on the actuator tube for covering the frame in its collapsed configuration.

In an alternative embodiment of the tissue manipulator, the frame includes a connector sleeve slidably mounted on the support shaft and located at a position beyond the distal end of the actuator tube. A pair of elongated flexible struts extends from the connector sleeve with each of the struts being secured to an intermediate portion of one of the outer strips and being flexed outwardly when the fingers are expanded.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF PREFERRED EMBODIMENTS

Figure 1:
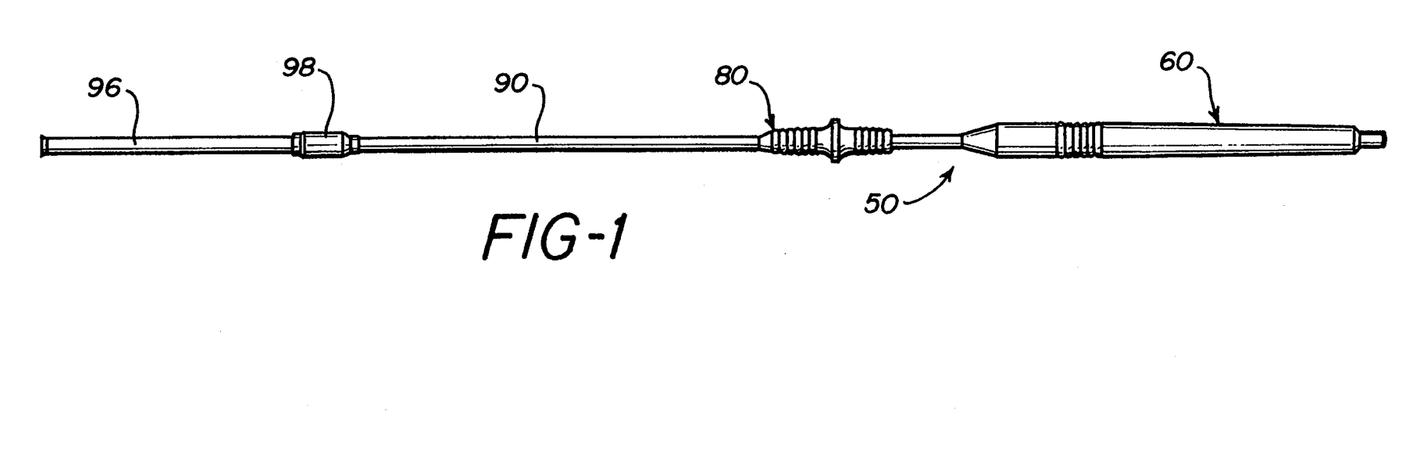
FIG. 1 is a side view of an endoscopic tissue manipulator constructed in accordance with this invention.
Figures 4, 5:
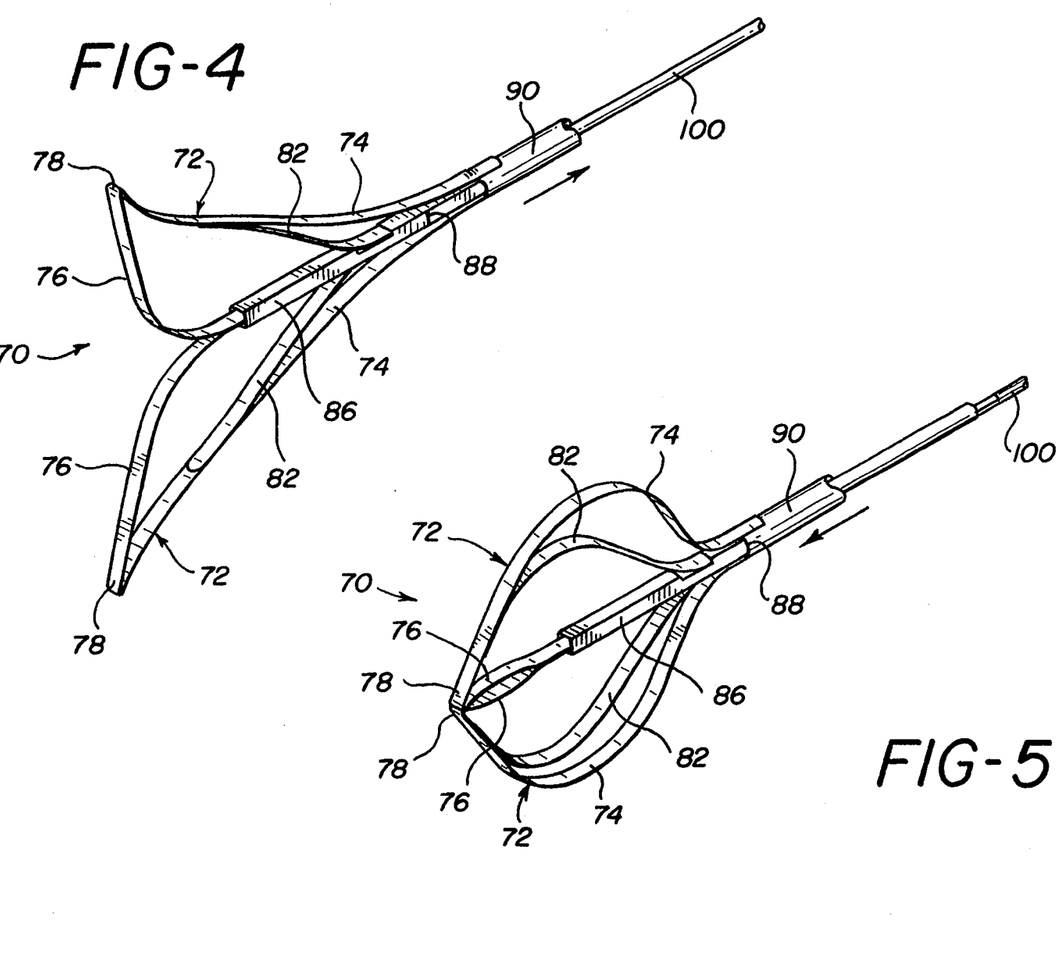
FIG. 4 is a perspective view showing the tissue manipulating platform expanded into a tulip-shaped configuration.
FIG. 5 is a perspective view showing the tissue manipulating platform expanded into a bulb-shaped configuration.

Referring to FIG. 1, the present invention is embodied in an endoscopic tissue manipulator, generally 50, which is insertable through a trocar tube or cannula to enable a surgeon to manipulate tissue inside a body cavity. The endoscopic tissue manipulator 50 is particularly suitable for use by a surgeon to displace large body organs, e.g., the liver, stomach or intestines, to enable surgery to be performed at a desired surgical site. The tissue manipulator 50 includes a proximal handle assembly 60 and a distal platform 70 which is expandable, after insertion inside the body, into a tulip-shaped configuration (FIG. 4) or a bulb-shaped configuration (FIG. 5). In either of its expanded configurations, the platform 70 can be used in spatula-like fashion to manipulate tissue, e.g., large body organs, inside the body. A finger operated actuator or slide 80 is connected to an elongated actuator tube 90 which is slidable relative to handle assembly 60 for expanding the platform 70 into the desired configuration. A sheath 96 is slidably mounted on the actuator tube 90 for covering the platform 70 prior to the insertion of the tissue manipulator 50 into the trocar tube or cannula.

Figure 3:
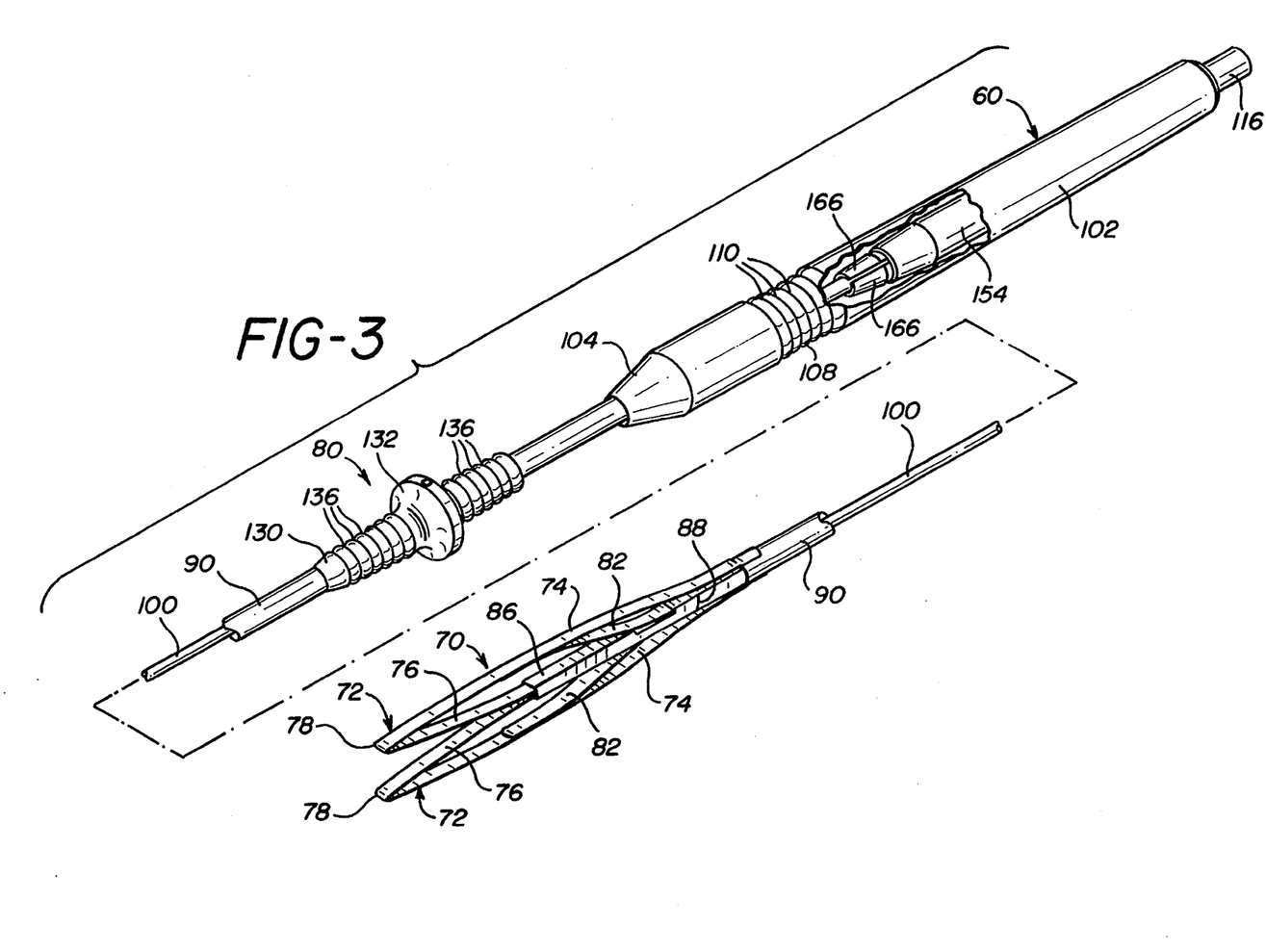
FIG. 3 is a partially cutaway perspective view of the tissue manipulator.

As shown in FIG. 3, the platform 70 consists of a plurality of flexible, interconnected strips which provide a pair of fingers 72 adapted to expand bilaterally outward when the finger slide 80 is actuated. Each of the fingers 72 comprises an elongated, flat metal strap which is folded or bent back upon itself to provide an outer strip 74 and an inner strip 76 which meet at a distal finger tip 78. The outer strip 74 is attached, e.g., by spot welding, to the distal end of the actuator tube 90. Also, the inner strip 76 is attached, e.g., by spot welding, to the distal end of a shaft or push rod 100 inside of the actuator tube 90. Each finger 72 includes a flexible strut 82 with its distal end secured to an intermediate portion of the outer strip 74 adjacent to the finger tip 78. Each strut 82 has its proximal end attached to a connector sleeve 84 (FIG. 7) which is slidably mounted on the inner strips 76 of the fingers 72 and is located at a position beyond the distal end of the actuator tube 90. The connector sleeve 84 is located within a guide tube 86 which is slidably received in the distal end of the actuator tube 90. The guide tube 86 is made, for example, of clear plastic material. The connector sleeve 84 and guide tube 86 slidably receive the inner strips 76 of the fingers 72. The guide tube 86 is attached to the connector sleeve 84 by the struts 82 which extend outwardly from the connector sleeve 84 through openings provided on opposite sides of the guide tube 86.

In the preferred embodiment, each expandable finger 72 includes an elongated, flat metal strap which is folded back upon itself by bending the strap about a round form to define a rounded corner at the finger tip 78. For example, a strap which is 0.100 inch in width and 0.008 inch in thickness is used to form the outer strip 74 and the inner strip 76 of each finger 72. The longitudinal edges of the strap are rounded to avoid the possibility of damage to the tissue. Each strut 82 is formed of the same strap material. Also, a nylon covering (not shown) is applied to all tissue engaging surfaces of the outer strips 74, the inner strips 76, and the struts 82 of the platform 70. To blunt the finger tips 78, a double thickness of the nylon covering is applied to the outer strips 74 and the inner strips 76 adjacent to the finger tips 78. The nylon covering is also applied to the outer surface of the actuator tube 90.

Referring to FIG. 4, when actuator tube 90 is retracted, i.e., moved proximally relative to the support shaft 100, the fingers 72 are spread apart and the platform 70 is expanded into a tulip-shaped configuration. The outer strips 74 are pulled in the proximal direction by the actuator tube 90 and the guide tube 86 is moved proximally along the inner strips 76 by the struts 82. The outer strips 74 are flexed outwardly and the inner strips 76 are bent laterally outward in opposite directions. Also, the struts 82 are flexed outwardly along with the outer strips 74. As a result, the fingers 72 are expanded bilaterally outward to form a spatula-like platform 70 of tulip-shaped configuration with the finger tips 78 spread apart. The tulip-shaped platform can be employed in a spatula-like fashion to displace large body organs, e.g., the liver, lungs and bowels, away from a desired surgical site.

Referring to FIG. 5, when the actuator tube 90 is advanced, i.e., moved distally relative to the support shaft 100, the fingers 72 are pressed together and the platform 70 is expanded into a bulb-shaped configuration. The outer strips 74 are pushed in the distal direction by the actuator tube 90 which engages a lip 88 on the outside of the guide tube 86 to advance the connector sleeve 84 and the guide tube 86 along the inner strips 76. The guide tube 86 maintains the inner strips 76 in alignment while the finger tips 78 are pressed together. The outer strips 74 are bowed laterally outward in opposite directions and the struts 82 are bowed outwardly along with the outer strips 74. As a result, the fingers 72 expand bilaterally outward to form a spatula-like platform 70 of bulb-shaped configuration with the finger tips 78 pressed together. The bulb-shaped platform allows the tissue to be manipulated inside a body cavity in situations where less space is available to accommodate the tissue manipulator 50. The guide tube 86 provides an anti-crossover mechanism which retains the finger tips 78 together when the platform 70 is expanded into its bulb-shaped configuration and prevents the possibility of misalignment and crossover of the finger tips 78 relative to each other.

The purpose of the struts 82 is to provide for shape control of the expanded platform 70. The struts 82 can be varied in length and attached at different positions to the outer strips 74 to vary the shape assumed by the platform 70 when it is expanded into its tulip-shaped configuration or its bulb-shaped configuration. Also, to vary the shape of the platform 70, the distal end of the support shaft 100 can be located closer to the connector sleeve 84 to allow the shaft 100 to engage and advance the connector sleeve 84 along the inner strips 76 as the platform 70 is expanded into its tulip-shaped configuration.

Figure 2:
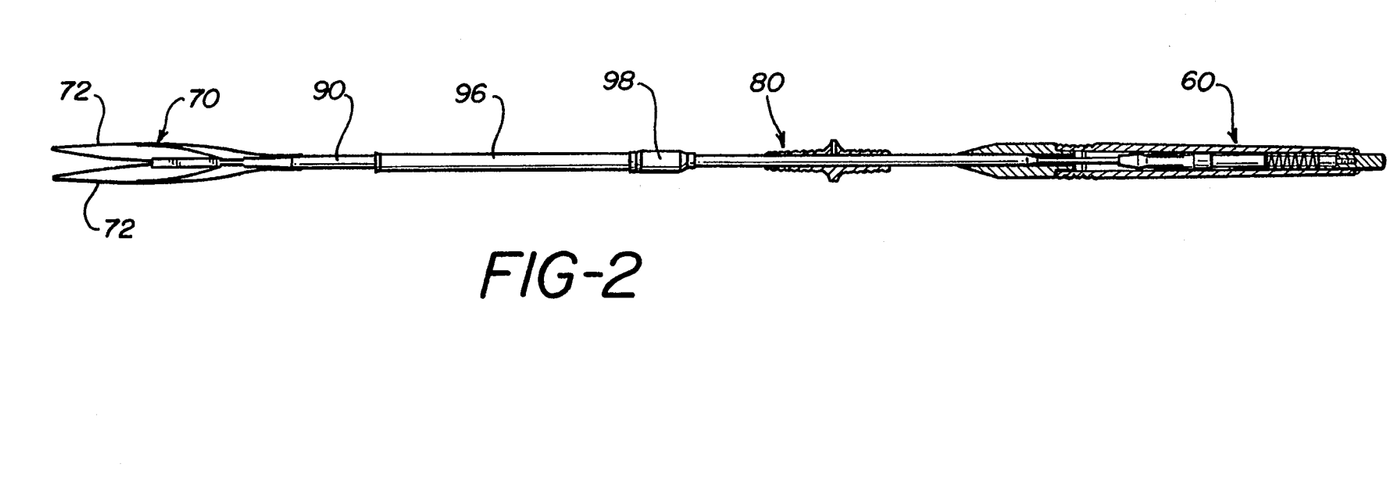
FIG. 2 is a partially cutaway side view of the tissue manipulator of FIG. 1 with its tissue manipulating platform exposed.

As shown in FIG. 1, the sheath 96 comprises an elongated tubular sleeve attached to a tubular grommet 98 slidably mounted on the actuator tube 90. Preferably, the sheath 96 consists of clear plastic material. In FIG. 2, the sheath 96 is retracted and the platform 70 is collapsed with the finger tips 78 spread slightly apart. In FIG. 1, the sheath 96 is advanced to cover the platform 70 in its collapsed configuration.

Figure 6:
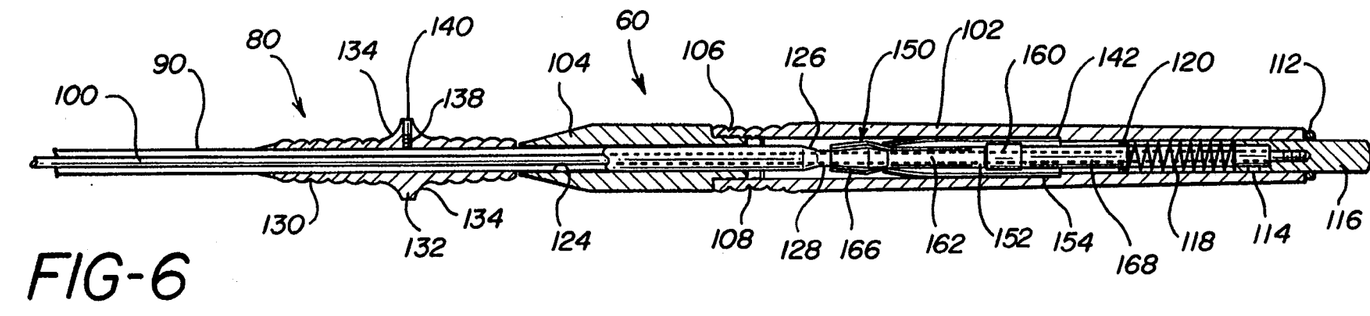
FIG. 6 is an enlarged longitudinal section of the handle of the tissue manipulator showing its finger slide retracted.

As shown in FIG. 6, the handle assembly 60 includes an elongated tubular handle 102 which is tapered from its distal end to its proximal end. A conical bushing 104 has a threaded sleeve 106 which is threadably secured to the distal end of the handle 102. The outer surface of the handle 102 has a concave circumferential indentation 108 which provides a finger grip adjacent to the distal end of the handle 102. A plurality of annular grooves 110 (FIG. 3) is provided on the surface area of the indentation 108 for convenience in the gripping of the handle 102.

The handle assembly 60 includes a collar 112 having a tubular sleeve 114 which is inserted into the proximal end of the handle 102. A hollow cylindrical push button 116 is slidably mounted within the sleeve 114 and projects rearwardly from the collar 112. The push button 116 is threadably connected to the proximal end of the shaft or push rod 100. A compression spring 118 is located within the sleeve 114 and is interposed between the push button 116 and an internal annular stop 120 provided at the distal end of the sleeve 114 to bias the push button 116 proximally relative to the handle 102.

Figure 7:
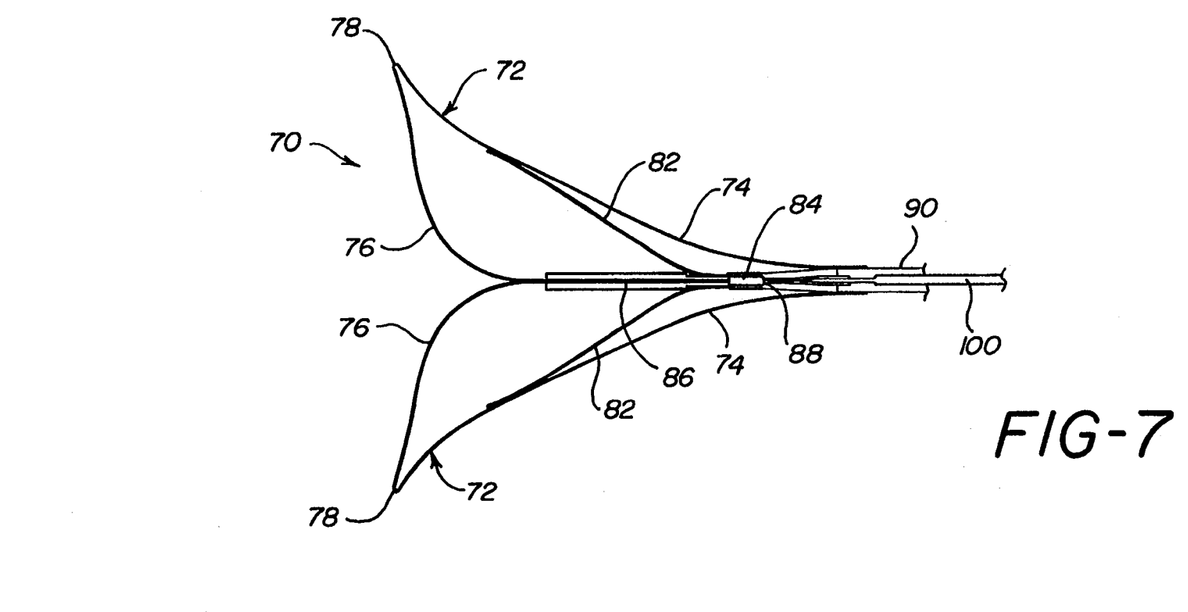
FIG. 7 is an enlarged side view of the tissue manipulating platform in its tulip-shaped configuration.

The elongated support shaft or push rod 100 extends axially through the elongated actuator tube 90 from the handle assembly 60 (FIG. 6) through the finger slide 80 to the platform 70 (FIG. 7). The actuator tube 90 is slidably received within an axial bore 124 in the conical bushing 104. The actuator tube 90 includes a conically tapered section 126 terminating at an elongated extension 128 of reduced diameter which slidably mounts the actuator tube 90 on the support shaft 100.

As shown in FIG. 3, the finger slide 80 has a generally cylindrical body 130 provided with an enlarged circular flange 132 projecting radially outward from the cylindrical body 130 to provide a convenient finger grip. The circular flange 132 is provided with gradually curved surfaces 134 (FIG. 6) on its opposite sides which merge with the cylindrical body 130 for comfort in gripping the flange 132. A plurality of annular grooves 136 is provided on the cylindrical body 130 for enhanced gripping of the finger slide 80. A set screw 138 is threaded into in a radial passage 140 in the flange 132 to secure the finger slide 80 to the actuator tube 90.

Figure 10:
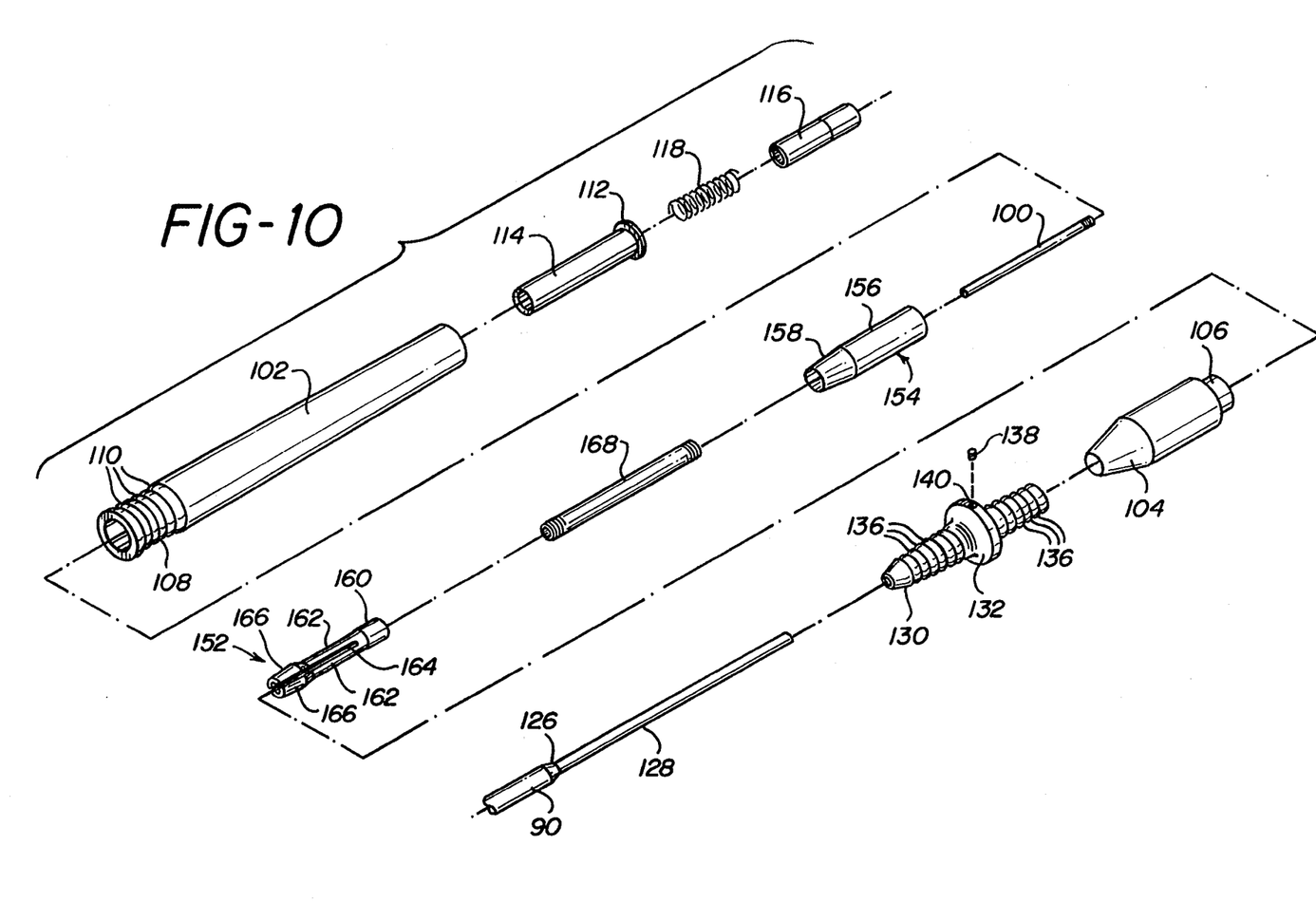
FIG. 10 is an exploded perspective view showing the components of the handle and finger slide of the endoscopic tissue manipulator.

Referring to FIG. 6, the handle assembly 60 includes a collet mechanism, generally 150, for releaseably engaging the extension 128 of the actuator tube 90 to retain the platform 70 in any configuration selected by operation of the finger slide 80. The collet mechanism 150 includes an elongated collet 152 which is slidably mounted for axial movement relative to a tubular collet housing 154 mounted within the tubular handle 102 in abutment with an annular ledge 142 provided on the inside of the handle 102. The collet housing 154 has a knurled outer surface 156 (FIG. 10) which engages the inner surface of the handle 102 to retain the collet housing 154 in place. The collet housing 154 has a tapered nose 158 for actuating the collet 152. The collet 152 has an internally threaded sleeve 160 provided with a plurality of elongated spring-like arms 162 separated by a set of longitudinal slots 164. The spring-like arms 162 terminate in a set of clamping fingers 166 which are slidably engaged by the tapered nose 158 of the collet housing 154 and clamped against the extension 128 of the actuator tube 90.

As shown in FIG. 6, the collet 152 is threadably attached to a connecting tube 168 which, in turn, is threadably secured to the push button 116. The push button 116 and the connecting tube 168 are biased in the proximal direction by the compression spring 118 to urge the clamping fingers 166 of the collet 152 into engagement with the tapered nose 158 of the collet housing 154. As a result, the clamping fingers 166 are normally clamped against the elongated extension 128 to prevent movement of the actuator tube 90 relative to the handle 102. The extension 128 is clamped by the collet mechanism 150 with sufficient frictional force to resist the spring forces generated in the expanded platform 70 by the flexing of the outer strips 74, the inner strips 76 and the struts 82. When the push button 116 is depressed, the connecting tube 168 and the collet 152 are advanced in the distal direction and the clamping fingers 166 are disengaged from the tapered nose 158 of the collet housing 154. As a result, the clamping fingers 166 are unclamped from the elongated extension 128 to allow the actuator tube 90 to return to its normal position with the platform 70 in its relaxed configuration.

In the operation of the present invention, an endoscope is inserted into a body cavity through an endoscopic tube, e.g., a trocar sleeve, extending through an incision made at the surface of the body. The endoscopic tube may include a trocar for piercing the body tissue to enable the tip of the endoscopic tube to be positioned adjacent to a desired surgical site to be observed or treated. After the endoscopic tube is positioned at the desired location, the trocar is withdrawn to allow the tissue manipulator 50 to be inserted into the body cavity through the working passage of the endoscope. Alternatively, the tissue manipulator 50 can be inserted into a separate endoscopic tube extending through another incision into the body cavity adjacent to the surgical site.

Next, the tissue manipulator 50 with its protective sheath 96 covering the expandable platform 70, is inserted into the passage in the endoscope and is advanced toward the surgical site by pushing on the handle assembly 60 to slide the tissue manipulator along the passage. The sheath 96 is sized to permit its insertion into the passage of the endoscope to protect the platform 70 and the endoscopic passage against damage. The grommet 98 has a larger diameter to preclude its entry into the passage of the endoscope. Thus, the grommet 98 is stopped at the entrance of the passage to retain the sheath 96 at the proximal end of the passage. As the tissue manipulator 50 is advanced along the passage, the platform 70 is moved distally out of the sheath 96. Eventually, the platform 70 emerges from the distal end of the passage where it is positioned adjacent to the desired surgical site. The tissue manipulator 50 can be rotated by 360 degrees about its axis by grasping and rotating the handle assembly 60 or the finger slide 80 to rotationally position the platform 70 in any desired orientation.

When it is desired to expand the platform 70, the surgeon grasps the finger slide 80 with his thumb and forefinger while holding the handle assembly 60 with the remaining fingers in one hand. By pulling the finger slide 80 proximally, as shown in FIG. 6, the actuator tube 90 is retracted relative to the shaft 100 to expand the platform 70 into its tulip-shaped configuration (FIG. 7). The extension 128 of the actuator tube 90 is retracted in the proximal direction and is held by the clamping fingers 166 of the collet mechanism 150 in any position selected by movement of the finger slide 80. As a result, the platform 70 is infinitely adjustable in size between its collapsed configuration (FIG. 3) and its fully expanded, tulip-shaped configuration (FIG. 4).

Figure 8:
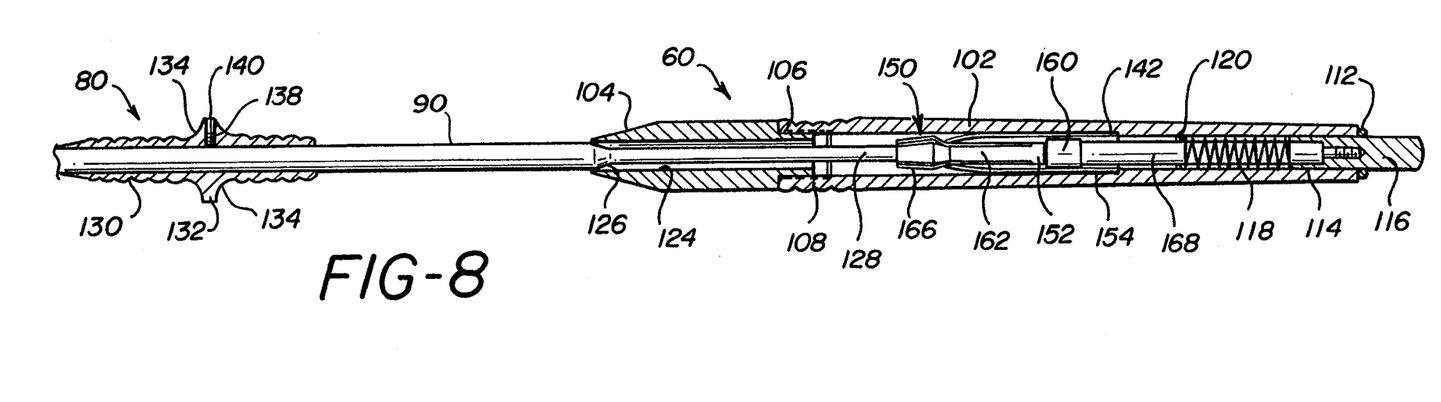
FIG. 8 is an enlarged longitudinal section of the handle of the tissue manipulator showing its finger slide advanced.
Figure 9:
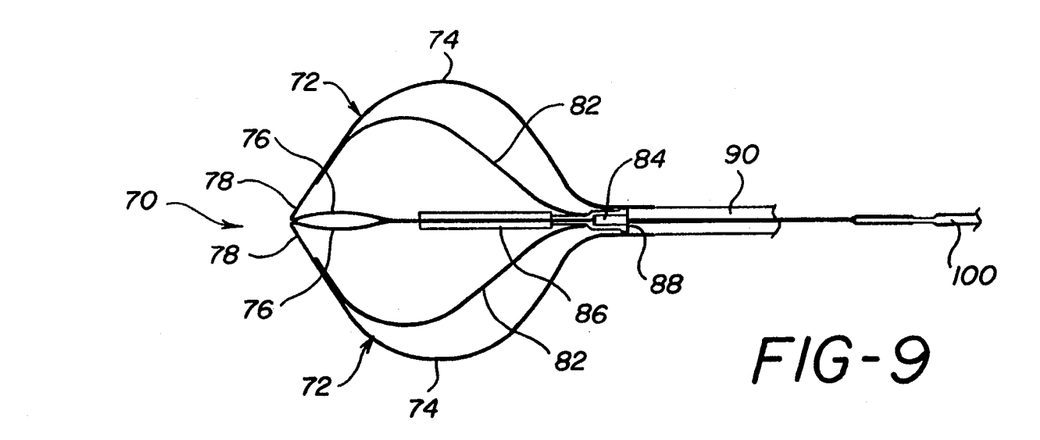
FIG. 9 is an enlarged side view of the tissue manipulating platform in its bulb-shaped configuration.

On the other hand, by pushing the finger slide 80 distally, as shown in FIG. 8, the actuator tube 90 is advanced to expand the platform 70 into its bulb-shaped configuration (FIG. 9). The extension 128 of the actuator tube 90 is advanced in the distal direction and is held by the clamping fingers 166 of the collet mechanism 150 in any position selected by movement of the finger slide 80. As a result, the collet mechanism 150 allows the platform 70 to be infinitely adjusted in size between its collapsed configuration (FIG. 3) and its fully expanded bulb-shaped configuration (FIG. 5).

After the platform 70 is expanded to the desired size and shape, the tissue manipulator can be used in a spatula-like manner to engage a large body organ, e.g., the liver, stomach or intestines, adjacent to the desired surgical site in the body cavity. The expanded platform 70 has a generally planar configuration which provides two flat tissue manipulating surfaces on its opposite sides. The spatula-like platform 70 is oriented with one of its flat surfaces engaged with the large body organ. Then, by pressing in a lateral direction on the handle assembly 60, the planar platform 70 can be urged against the large body organ, in a manner similar to the use of a spatula, to displace or to retain the large body organ in a desired position away from the surgical site.

When it is desired to remove the tissue manipulator from the endoscope, the platform 70 is returned to its collapsed configuration by pressing the push button 116 which releases the collet mechanism 150. As a result, the clamping fingers 166 of the collet mechanism 150 are disengaged from the extension 128 of the actuator tube 90. The spring forces generated by the flexed strips 174 and 176 and the struts 182 of the expanded platform 70 are released allowing the platform 70 to return to its collapsed configuration (FIG. 3). Then, by grasping and pulling the handle assembly 60, the tissue manipulator 50 is removed from the working passage of the endoscope.

Figures 11, 12, 13:
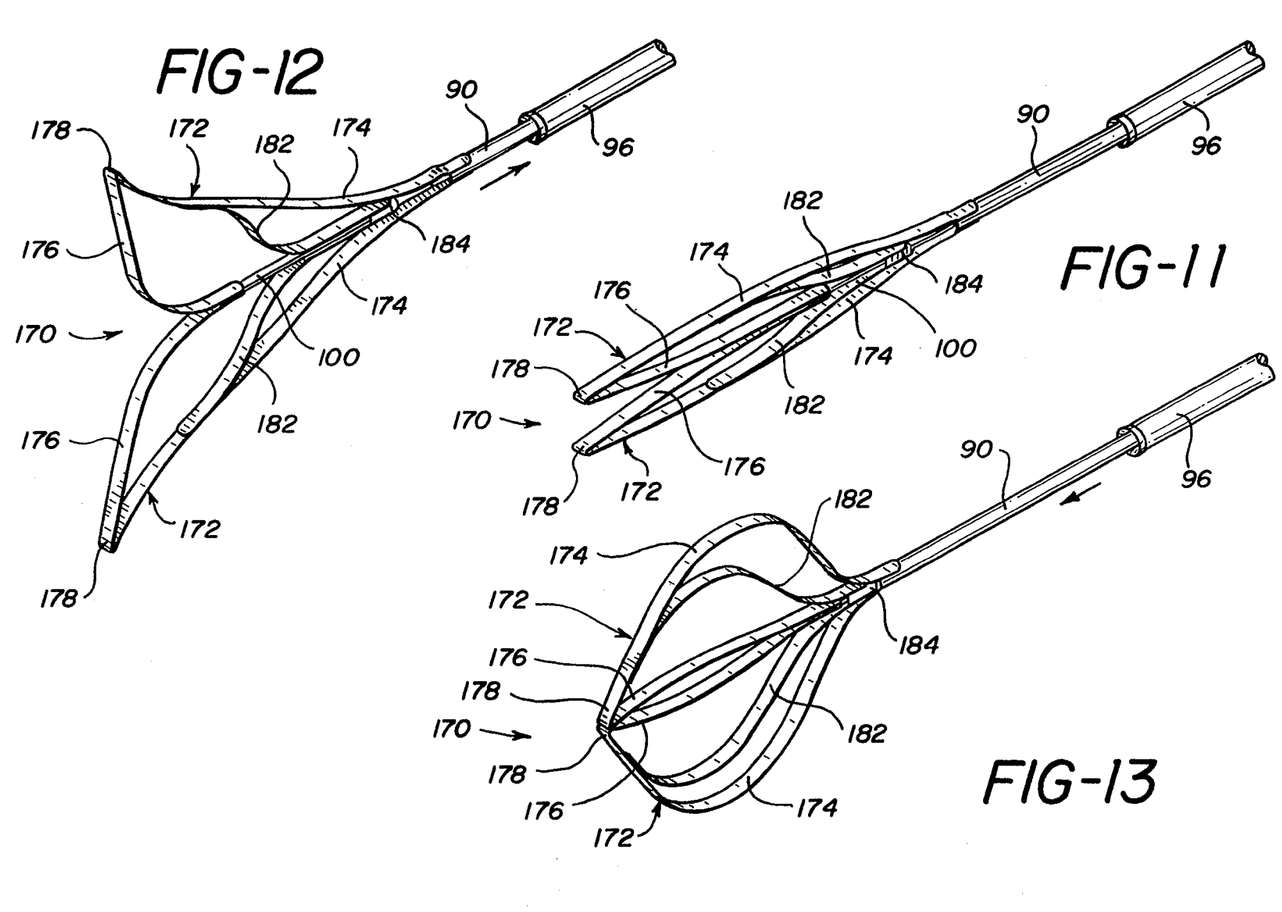
FIG. 11 is a perspective view showing an alternative embodiment of the tissue manipulator.
FIG. 12 is a perspective view of the tissue manipulator of FIG. 11 showing its tulip-shaped configuration.
FIG. 13 is a perspective view of the tissue manipulator of FIG. 11 showing its bulb-shaped configuration.

An alternative embodiment of the tissue manipulator shown in FIG. 11 includes a platform 170 consisting of a plurality of flexible, interconnected strips which provide a pair of fingers 172 adapted to expand bilaterally outward to provide a spatula-like platform for manipulating tissue. Each of the fingers 172 comprises an elongated, flat metal strap which is folded or bent back upon itself to provide an outer strip 174 and an inner strip 176 which meet at a distal finger tip 178. The outer strip 174 is attached, e.g., by spot welding, to the distal end of the actuator tube 90. Also, the inner strip 176 is attached, e.g., by spot welding, to the distal end of the support shaft 100 which, as shown in FIG. 11, extends outwardly beyond the distal end of the actuator tube 90. Each finger 172 includes a flexible strut 182 with its distal end secured to an intermediate portion of the outer strip 174 adjacent to the finger tip 178. Each strut 182 has its proximal end attached to a connector sleeve 184 which is slidably mounted on the support shaft 100 and is located at a position beyond the distal end of the actuator tube 90.

Referring to FIG. 12, when actuator tube 90 is retracted, i.e., moved proximally relative to the support shaft 100, the fingers 172 are spread apart and the platform 170 is expanded into a tulip-shaped configuration. The outer strips 174 are pulled in the proximal direction by the acutator tube 90 and the connector sleeve 184 is moved proximally along the inner strips 176 by the struts 182. The outer strips 174 are flexed outwardly and the inner strips 176 are bent laterally outward in opposite directions. Also, the struts 182 are flexed outwardly along with the outer strips 174. As a result, the fingers 172 are expanded bilaterally outward to form a spatula-like platform 170 of tulip-shaped configuration with the finger tips 178 spread apart.

Referring to FIG. 13, when the actuator tube 90 is advanced, i.e., moved distally relative to the support shaft 100, the fingers 172 are pressed together and the platform 170 is expanded into a bulb-shaped configuration. The outer strips 174 are pushed in the distal direction by the actuator tube 90 which advances the connector sleeve 184 along the inner strips 176. The outer strips 174 are bowed laterally outward in opposite directions and the struts 182 are bowed outwardly along with the outer strips 174. Also, the inner strips 176 are bowed slightly outward while the finger tips 178 are pressed together. As a result, the fingers 172 expand bilaterally outward to form a spatula-like platform 170 of bulb-shaped configuration with the finger tips 178 pressed together.

The invention in its broader aspects is not limited to the specific details of the preferred embodiments shown and described, and those skilled in the art will recognize that the invention can be practiced with modification within the spirit and scope of the appended claims.

We claim:

1. An endoscopic tissue manipulator, comprising:
   a handle;
   a support shaft extending from said handle;
   a tube slidably mounted on said support shaft for longitudinal movement relative to said support shaft; and
   an expandable frame mounted at the distal end of said support shaft and connected to said tube, said frame being expandable by movement of said tube relative to said support shaft to provide a platform for manipulating tissue wherein said frame includes
   a pair of expandable fingers each comprising a flexible outer strip secured to the distal end of said tube and a flexible inner strip secured to the distal end of said support shaft, said inner and outer strips being joined together at a distal finger tip; and
   said fingers being flexed laterally outward in opposite directions by axial movement of said tube relative to said shaft to provide a platform for engaging the tissue.

2. The tissue manipulator of claim 1, wherein:
   said fingers are expandable into a tulip-shaped configuration with said finger tips spread apart and into a bulb-shaped configuration with said finger tips together.

3. The tissue manipulator of claim 2, wherein:
   said fingers are expandable to said tulip-shaped configuration by movement of said tube proximally relative to said support shaft and to said bulb-shaped configuration by movement of said tube distally relative to said support shaft.

4. The tissue manipulator of claim 1, wherein said frame includes:
   a connector sleeve slidably mounted on said inner strips and located at a position beyond the distal end of said tube; and
   a pair of elongated flexible struts extending from said connector sleeve, each of said struts being secured to an intermediate portion of one of said outer strips and being flexed outwardly when said fingers are expanded.

5. The tissue manipulator of claim 4, which includes:
   a guide tube extending distally from said connector sleeve for slidably receiving said inner strips therein, said guide tube serving to hold said inner strips together when said actuator tube is advanced to prevent misalignment and crossover of said finger tips.

6. The tissue manipulator of claim 1, wherein said frame includes:
   a connector sleeve slidably mounted on said support shaft and located at a position beyond the distal end of said tube; and
   a pair of elongated flexible struts extending from said connector sleeve, each of said struts being secured to an intermediate portion of one of said outer strips and being flexed outwardly when said fingers are expanded.

7. The tissue manipulator of claim 1, wherein:
   each of said fingers comprises an elongated strap which is folded back upon itself to define said inner and outer strips.

8. An endoscopic tissue manipulator for insertion into an endoscopic tube for manipulating tissue in a body cavity, comprising:
   a handle;
   a support shaft extending from said handle;
   an actuator tube slidably mounted on said support shaft for longitudal movement relative to said support shaft; and
   a tissue manipulating frame mounted at the distal end of said support shaft and connected to said actuator tube, said frame having a collapsed configuration for insertion through the endoscopic tube, and said frame being expandable by movement of said actuator tube relative to said shaft to provide a platform for manipulating the tissue in the body cavity wherein said frame includes
   a pair of expandable fingers each comprising a flexible outer strip secured to the distal end of said actuator tube and a flexible inner strip secured to the distal end of said support shaft, said inner and outer strips being joined together at a distal finger tip; and
   said fingers being flexed laterally outward in opposite directions by axial movement of said acutator tube relative to said shaft to provide a platform for engaging the tissue.

9. The tissue manipulator of claim 8, wherein:

said fingers are expandable into a tulip-shaped configuration with said finger tips spread apart and into a bulb-shaped configuration with said finger tips together.

10. The tissue manipulator of claim 9, wherein:

said fingers are expandable to said tulip-shaped configuration by movement of said actuator tube proximally relative to said support shaft and to said bulb-shaped configuration by movement of said actuator tube distally relative to said support shaft.

11. The tissue manipulator of claim 8, wherein said frame includes:

a connector sleeve slidably mounted on said inner strips and located at a position beyond the distal end of said actuator tube; and a pair of elongated flexible struts extending from said connector sleeve, each of said struts being secured to an intermediate portion of one of said outer strips and being flexed outwardly when said fingers are expanded.

12. The tissue manipulator of claim 11, which includes:

a guide tube extending distally from said connector sleeve for slidably receiving said inner strips therein, said guide tube acting to hold said inner strips together when said actuator tube is advanced to prevent misalignment and crossover of said finger tips.

13. The tissue manipulator of claim 8, wherein said frame includes:

a connector sleeve slidably mounted on said support shaft and located at a position beyond the distal end of said actuator tube; and a pair of elongated flexible struts extending from said connector sleeve, each of said struts being secured to an intermediate portion of one of said outer strips and being flexed outwardly when said fingers are expanded.

14. The tissue manipulator of claim 8, wherein:

each of said fingers comprises an elongated strap which is folded back upon itself to define said inner and outer strips.

15. The tissue manipulator of claim 8, which includes:

a manually operable slide connected to said actuator tube for advancing and retracting said actuator tube axially relative to said handle.

16. The tissue manipulator of claim 15, which includes:

collet means on said handle for releaseably engaging said actuator tube to retain said platform in an expanded configuration.

17. The tissue manipulator of claim 16, which includes:

a manually operable release button on said handle for releasing said collet means to disengage said actuator tube and allow said platform to return to its collapsed configuration.

18. The tissue manipulator of claim 8, which includes:

a sheath slidably mounted on said actuator tube for covering said frame in its collapsed configuration.

* * * * *